(12) United States Patent
Hill et al.

(10) Patent No.: US 9,159,532 B2
(45) Date of Patent: Oct. 13, 2015

(54) METHOD OF ANALYZING A SAMPLE AND CHARGED PARTICLE BEAM DEVICE FOR ANALYZING A SAMPLE

(71) Applicant: Carl Zeiss Microscopy Ltd., Cambridge (GB)

(72) Inventors: Edward Hill, St. Ives (GB); Stewart Bean, Wyton (GB)

(73) Assignee: Carl Zeiss Microscopy Ltd., Cambridge (GB)

( * ) Notice: Subject to any disclaimer, the term of this patent is extended or adjusted under 35 U.S.C. 154(b) by 95 days.

(21) Appl. No.: 14/150,012

(22) Filed: Jan. 8, 2014

(65) Prior Publication Data
US 2014/0197310 A1  Jul. 17, 2014

(30) Foreign Application Priority Data
Jan. 15, 2013 (EP) .................................... 13151344

(51) Int. Cl.
*H01J 37/26* (2006.01)
*G01N 23/225* (2006.01)

(52) U.S. Cl.
CPC ............ *H01J 37/26* (2013.01); *G01N 23/2254* (2013.01); *H01J 2237/2804* (2013.01); *H01J 2237/2806* (2013.01); *H01J 2237/2808* (2013.01); *H01J 2237/2809* (2013.01)

(58) Field of Classification Search
USPC ......................................... 250/307, 306, 310
See application file for complete search history.

(56) References Cited

U.S. PATENT DOCUMENTS

2012/0281883 A1    11/2012 Hurley et al.
2014/0092230 A1*   4/2014 Langer et al. .................. 348/80

FOREIGN PATENT DOCUMENTS

WO    WO 2012/118866    9/2012
WO    WO 2012/174173    12/2012

OTHER PUBLICATIONS

Ward, "Analysis and significance of mineral matter in coal seams," International Journal of Coal Geology 50 (2002) 135-168.
Hill et al., "Cleaner and more efficient coal utilization driven by automated quantification of inherent and extraneous mineral matter," published at conference "Process Mineralogy '12", Cape Town (South Africa) Nov. 2012.
Struers brochure, "Cold Mounting", Ballerup (Denmark), Oct. 2008.
MacRae et al., "Quantitative Cathodoluminescence ," Microscopy and Microanalysis, vol. 15, No. 3, 222-230 (2009).
Extended European Search Report for corresponding EP Appl No. 13151344.2, dated Jun. 21, 2013.
Creelman et al., "A scanning electron microscope method for automated, quantitative analysis of mineral matter in coal," International Journal of Coal Geology 30 (1996), 249-269.

* cited by examiner

*Primary Examiner* — Kiet T Nguyen
(74) *Attorney, Agent, or Firm* — Fish & Richardson P.C.

(57) ABSTRACT

The invention refers to a method and a charged particle beam device for analyzing an object using a charged particle beam interacting with the object. The object comprises a sample embedded in a resin. Interaction radiation in the form of cathodoluminescence light is detected for identifying areas in which the resin is arranged and in which the sample is arranged. Interaction particles are detected to identify particles within the resin and the sample for further analysis by using EDX analysis.

20 Claims, 4 Drawing Sheets

METHOD OF ANALYZING A SAMPLE AND CHARGED PARTICLE BEAM DEVICE FOR ANALYZING A SAMPLE

This application refers to a method of analyzing a sample using a charged particle beam device and to a charged particle beam device for analyzing a sample.

It is often important to know the composition of materials used in different fields of technology. One of those materials is coal. Coal is, for example, one important source of global electricity production. In particular, coal is burned for providing energy to drive steam turbines which generate electricity. Coal mainly consists of carbon from plant material and naturally contains minerals. The mineral content of coal can be as high as 30% of the composition of coal. Minerals present in coal are, for example, silicate, clays, carbonates, oxides and sulphides. The exact quantities of the minerals in the coal may vary.

The minerals in coal are often incombustible and cause negative side effects. In particular, they reduce the coal's heating value and end up as ash particulates which contribute to the reason for health problems in the form of asthma or bronchitis. Moreover, the ash which results from the combustion of minerals accumulates on heat-transfer surfaces of parts of a power plant. The ash has to be removed. Therefore, the ash results in an expensive down-time for maintenance of the power plant. Furthermore, the minerals also cause smog and produce nitrogen oxide as well as sulphur dioxide, which contribute to acid rain. Accordingly, it is desirable to get to know the accurate or detailed composition of coal.

The composition of samples such as coal may be examined by using electron beam devices, in particular a scanning electron microscope (also called SEM) and/or a transmission electron microscope (also called TEM). Those electron beam devices are used for examining samples in order to obtain insights with regard to the properties and behaviour of the samples under specific conditions. In the case of a SEM, an electron beam (also called primary electron beam) is generated using a beam generator and focused by a beam guiding system, in particular an objective lens, onto a sample to be examined. Using a deflection device, the primary electron beam is guided in a raster-type fashion over a surface of the sample to be examined. In this case, the electrons of the primary electron beam interact with the material of the sample to be examined. As a consequence of the interaction, in particular electrons are emitted from the surface of the sample to be examined (so-called secondary electrons) and electrons of the primary electron beam are backscattered (so-called backscattered electrons). The secondary electrons and backscattered electrons are detected and used for image generation. Imaging of the surface of the sample to be examined is thus obtained.

In the case of a TEM, a primary electron beam is likewise generated using a beam generator and focused by a beam guiding system onto a sample to be examined. The primary electron beam radiates through the sample to be examined. During the passage of the primary electron beam through the sample to be examined, the electrons of the primary electron beam interact with the material of the sample to be examined. The electrons passing through the sample to be examined are imaged onto a luminescence screen or onto a detector (for example a camera) by a system consisting of at least an objective lens and a projection lens system. In addition, electrons scattered or backscattered at the sample to be examined and/or secondary electrons emitted by the sample to be examined may be detected using further detectors in order to image the sample to be examined. In this case, the imaging is effected in the scanning mode of a TEM. A TEM of this type is generally designated as STEM.

A charged particle beam guided onto a sample, for example an electron beam, can, in addition to the interaction particles mentioned above, also interact with the sample in such a way that electromagnetic radiation arises. For example, the electromagnetic radiation may be in the form of X-rays. These X-rays may be detected by using energy dispersive X-ray spectroscopy (so called EDX) which provides the composition of the sample by identifying the materials comprised in the sample. The electromagnetic radiation may also be in the form of cathodoluminescence light. By detecting and evaluating the cathodoluminescence light (for example using an intensity and spectral analysis), it is possible to determine properties of the material of the sample.

It is known to use a SEM to analyze the composition of coal. For this purpose, a piece of coal is embedded in carnauba wax. The bedding made of carnauba wax fixes the position of the coal relative to the bedding made of carnauba wax. The coal and the bedding of carnauba wax are arranged on a sample holder which is introduced into the SEM. The use of carnauba wax may be problematic. It is known that arranging a sample in carnauba wax for examination with the SEM is not an easy process. Therefore, it often requires services of specialist laboratories which are expensive. Moreover, arranging the sample in carnauba wax is time consuming.

A natural or synthetic resin could be used as a bedding for the coal instead of carnauba wax. Since resin is easier to handle, arranging of the coal in resin would not be as expensive as arranging in carnauba wax. However, the resin and coal have similar average atomic weights. This makes it nearly impossible to clearly distinguish the coal and the resin in a SEM by detecting backscattered electrons. Due to the similar atomic weights, the contrast in the image provided by detecting backscattered electrons for coal and resin is more or less equal. It is not possible to identify the coal and the resin in the image and to differentiate between the coal and the resin.

Therefore, it is desirable to provide a method and a charged particle beam device which make it possible to use a bedding made of resin for examination of a sample, by using in particular backscattered electrons for imaging of the sample. According to the invention, this is solved by a method of analyzing an object using a charged particle beam device. The charged particle beam device comprises a charged particle source for generating a charged particle beam, an objective lens for focusing the charged particle beam onto the object, a first detector for detecting interaction radiation and a second detector for detecting interaction particles. The method comprises: providing the object comprising a sample and a resin by arranging the sample in the resin; generating the charged particle beam using the charged particle source; guiding the charged particle beam onto the sample and the resin using the objective lens; guiding the charged particle beam over the sample and the resin; generating interaction radiation emitted from the sample and the resin due to interaction of the charged particle beam with the sample as well as interaction of the charged particle beam with the resin; identifying a first area in which the resin is arranged and identifying a second area in which the sample is arranged by detecting the interaction radiation using the first detector; identifying a position of at least one particle of the resin in the first area or at least one particle of the sample in the second area by detecting interaction particles using the second detector wherein the interaction particles are generated by the interaction of the charged particle beam with the at least one particle of the resin or of the sample; and analyzing the at least one particle of the resin or of the sample using the charged particle beam. A computer readable medium storing computer software is given for analyzing an object using a charged particle beam device. The computer software comprises executable code which is run in a microprocessor, wherein the preceding method is carried out when the computer software is loaded in the microprocessor and the executable code is run in the microprocessor. A charged particle beam device according to the invention is given for analyzing an object. The charged particle beam device comprises: a charged particle source for generating a charged particle beam; an objective lens for focusing the charged particle beam onto the object; a first detector for detecting interaction radiation; a second detector for detecting interaction particles; a microprocessor; and a computer readable medium as described above. Further features of the invention are evident from the following description, the following claims and/or the accompanying figures.

A method according to the invention is used for analyzing an object comprising a sample using a charged particle beam device. The term "object" will be explained further below. The sample may comprise a particle which is to be analyzed. In other words, the method is for operating the charged particle beam device in such a way that a sample is analyzed. The charged particle beam device comprises a charged particle source for generating a charged particle beam, an objective lens for focusing the charged particle beam onto the sample, a first detector for detecting interaction radiation and a second detector for detecting interaction particles. The method according to the invention comprises several steps. In particular, the method comprises the step of providing the object by arranging the sample in a resin, for example a natural resin or a synthetic resin such as a resin known as SpeciFix-20 offered by the company Struers A/S (catalogue number 40200048). Therefore, the object comprises the resin and the sample embedded in the resin. Moreover, the charged particle beam is generated by using the charged particle source. The method according to the invention also comprises the step of guiding the charged particle beam onto the sample and the resin using the objective lens. Thus, the charged particle beam is guided onto the sample and onto the resin. Furthermore, the charged particle beam is guided over the sample and the resin. For example, the charged particle beam is guided over the sample and the resin in a raster-like manner. The method according to the invention also comprises generating interaction radiation emitted from the sample and the resin due to an interaction of the charged particle beam with the sample as well as an interaction of the charged particle beam with the resin. Furthermore, the method according to the invention also comprises the step of identifying a first area in which the resin is arranged and identifying a second area in which the sample is arranged by detecting the interaction radiation using the first detector. Additionally, a position of at least one particle of the resin in the first area and/or at least one particle of the sample in the second area is identified by detecting interaction particles using the second detector. The interaction particles are generated by the interaction of the charged particle beam with the at least one particle of the resin or of the sample. For example, the interaction particles are emitted by the at least one particle (for example secondary electrons) or backscattered from the at least one particle (for example backscattered electrons). The at least one particle of the resin or of the sample is analyzed using the charged particle beam.

The invention is not restricted to the order (sequence) of steps as mentioned above or mentioned further below. Alternatively, the order of the steps of the method according to the invention may be differently chosen with respect to one or more steps of the method according to the invention.

The invention is based on the finding that it is possible to identify the first area in which the resin used as a bedding for the sample is arranged and the second area in which the sample is arranged, by detecting interaction radiation using the first detector. The term "area" is not restricted to a specific size. To the contrary, any area having any suitable size may be used. The resin is normally a strong emitter in interaction radiation as compared to the sample (for example coal). Therefore, it is possible to identify the second area in which the sample is arranged and the first area in which the resin is arranged, and to create a map including these areas. The map identifies the first area and the second area so that it is known at which position the resin is arranged and at which position the sample is arranged. Therefore, the charged particle beam may be guided to the second area in which the sample is arranged for further examination and analysis of the sample or a part of the sample to be analyzed, for example by detecting backscattered particles. This allows for identifying the areas in which, for example, minerals are included in the sample and to further analyze those minerals, for example by using EDX. However, the method can also be used for analyzing particles being included not in the sample, but in the resin.

It is additionally or alternatively provided in an embodiment of the method according to the invention that the step of generating the interaction radiation comprises generating cathodoluminescence light. The resin, in particular the above mentioned kind of resins, is a strong emitter of cathodoluminescence light as compared to the sample to be analyzed. Therefore, it is possible to identify the first area in which the resin is arranged and the second area in which the sample is arranged.

It is additionally or alternatively provided in a further embodiment of the method according to the invention that the step of analyzing the at least one particle of the resin or of the sample comprises detecting electromagnetic radiation (for example X-rays) by using, for example, a third detector. This embodiment comprises, for example, the analysis of the sample using EDX.

It is additionally or alternatively provided in a further embodiment of the method according to the invention that the method comprises at least one of the following steps:

In a first step, the charged particle beam is scanned over an object comprising the resin and the sample embedded in the resin. Interaction radiation, in particular cathodoluminescence light, is detected by using the first detector. Signals of the first detector are used for generating a first image based on the interaction radiation.

In a second step, a first area of the object is identified or first areas of the object are identified which comprise(s) the resin by using the first detector detecting the interaction radiation.

In a third step, a second area is identified or second areas of the object are identified which comprise(s) the sample embedded in the resin by using the first detector detecting the interaction radiation.

In a fourth step, interaction particles generated by the interaction of the charged particle beam with the object (i.e. the resin and the sample embedded in the resin) are detected by using the second detector. The interaction particles may be secondary particles (such as secondary electrons) and/or backscattered particles (such as backscattered electrons). Signals generated by the second detector are used for generating a second image. In an embodiment of the method according to the invention, the fourth step and the first step are carried out in parallel.

In a fifth step, the positions of particles comprised in the resin and/or in the sample are identified by analyzing the second image. The particles may be minerals. However, the invention is not restricted to the analysis of minerals. Instead, any kind of particle can be analyzed.

In a sixth step, the particles comprised in the resin and/or in the sample are irradiated with the charged particle beam by guiding the charged particle beam to the identified positions of the particles. Interaction radiation (for example X-rays) is generated and detected using the third detector (for example, an EDX-detector). Signals of the third detector are used for generating a spectrum for each particle comprised in the resin and/or in the sample.

In a seventh step, the composition of at least one of the particles comprised in the resin and/or in the sample is identified by analyzing the spectrum generated for this at least one particle. Furthermore, it is identified whether this one particle is arranged within the sample, at the surface of the sample or in the resin.

The invention also refers to a computer readable medium storing computer software for analyzing an object using a charged particle beam device, the computer software comprising executable code which is run in a microprocessor. The method comprising at least one of the above or below mentioned steps or a combination of at least two of the above or below mentioned steps is carried out when the computer software is loaded in the microprocessor and the executable code is run in the microprocessor.

The invention also refers to a charged particle beam device for analyzing an object. The charged particle beam device comprises a charged particle source for generating a charged particle beam, an objective lens for focusing the charged particle beam onto the object, a first detector for detecting interaction radiation, a second detector for detecting interaction particles, a microprocessor and a computer readable medium as mentioned above or below. The method comprising at least one of the above or below mentioned steps or a combination of at least two of the above or below mentioned steps is carried out when the computer software stored on the computer readable medium is loaded in the microprocessor and the executable code is run in the microprocessor.

It is additionally or alternatively provided in an embodiment of the charged particle beam device according to the invention that the charged particle beam device is an electron beam device (for example a SEM). Alternatively, the charged particle beam device is an ion beam device.

The invention is explained in greater detail below on the basis of exemplary embodiments and using figures, in which.

Figure 1:
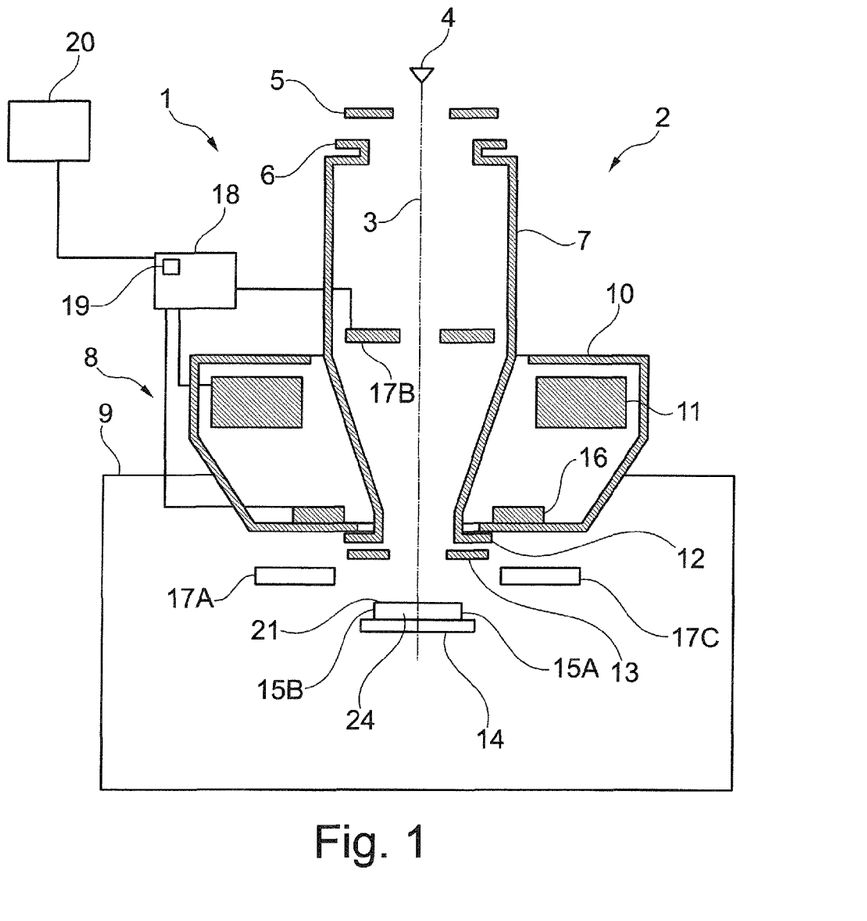
FIG. 1 shows a schematic illustration of an embodiment of the charged particle beam device according to the invention.

FIG. 1 shows a schematic illustration of a charged particle beam device 1 in the form of a SEM comprising a charged particle beam column 2, which is embodied as an electron beam column. However, it is expressly pointed out that the invention is not restricted to a SEM. Rather, the invention can be used for any charged particle beam device, in particular for an ion beam device.

The charged particle beam column 2 has an optical axis 3, a beam generator 4 in the form of an electron source (cathode), a first electrode 5 in the form of an extraction electrode, and a second electrode 6 in the form of an anode, which simultaneously forms one end of a beam guiding tube 7. By way of example, the beam generator 4 is a thermal field emitter. Electrons that emerge from the beam generator 4 are accelerated to anode potential due to a potential difference between the beam generator 4 and the second electrode 6. Accordingly, a charged particle beam in the form of an electron beam is provided.

Furthermore, the charged particle beam device 1 comprises an objective lens 8, which projects into a sample chamber 9 of the charged particle beam device 1. The objective lens 8 has a hole through which the beam guiding tube 7 is led. The objective lens 8 is furthermore provided with pole pieces 10, in which a coil 11 is arranged. An electrostatic retarding device is arranged downstream of the beam guiding tube 7. The electrostatic retarding device has a tube electrode 12 forming one end of the beam guiding tube 7. Furthermore, the electrostatic retarding device has a single electrode 13 arranged adjacent to the tube electrode 12 along the optical axis 3. A sample carrier 14 is arranged in the sample chamber 9. The sample carrier 14 carries an object 24 (for example a block sample) comprising a sample 15A to be examined and/or to be processed and a bedding made of a resin 15B. The sample 15A is arranged in the bedding made of the resin 15B.

The tube electrode 12 together with the beam guiding tube 7 is at anode potential, while the single electrode 13 and the object 24 comprising the sample 15A and the bedding made of the resin 15B are at a lower potential relative to the anode potential. In this way, the electrons of the charged particle beam can be decelerated to a desired energy required for the examination and/or processing of the object 24 comprising the sample 15A and the bedding made of the resin 15B. The charged particle beam device 1 comprises a first detector 17A for detecting cathodoluminescence light generated by an interaction of the charged particle beam with the object 24 comprising the sample 15A and the bedding made of the resin 15B. The signals generated by the first detector 17A are communicated via a signal line (not shown) to an electronic unit 18 comprising a microprocessor 19, which is made for acquiring signals, for generating images of at least a part of the object 24 and for transmitting the generated images to a monitor 20. The electronic unit 18 also comprises a computer readable medium storing computer software. The computer software comprises an executable code which is run in the microprocessor 19. The method according to the invention is carried out when the executable code is run in the microprocessor 19.

For imaging purposes, secondary electrons and/or backscattered electrons that arise on account of interactions of the charged particle beam with the object 24 comprising the sample 15A and the bedding made of the resin 15B are detected by using a second detector 17B arranged in the beam guiding tube 7. The second detector 17B is also connected with the electronic unit 18 for communicating signals for imaging purposes. In an alternative embodiment the second detector 17B is arranged between the single electrode 13 and the object 24, and the second detector 17B is used for detecting backscattered electrons.

The charged particle beam device 1 also comprises a third detector 17C for detecting X-rays generated by an interaction of the charged particle beam with the object 24 comprising the sample 15A and the bedding made of the resin 15B. The third detector 17C is used for material analysis using EDX and is connected with the electronic unit 18 via a signal line (not shown) for communicating signals.

The charged particle beam column 2 additionally comprises a scanning device 16, which deflects the charged particle beam, such that the charged particle beam can be scanned over the object 24 comprising the sample 15A and the bedding made of the resin 15B arranged on the sample carrier 14. The scanning device 16 is connected to the electronic unit 18 and the microprocessor 19 thereof for the purpose of controlling scanning of the charged particle beam over a (scanning) surface 21 of the object 24 comprising the sample 15A and the bedding made of the resin 15B.

The objective lens 8 focuses the charged particle beam onto the surface 21 of the object 24 comprising the sample 15A and the bedding made of the resin 15B. For this purpose, the coil 11 of the objective lens 8 is connected to the electronic unit 18. The electronic unit 18 drives the coil 11 and thus ensures that the charged particle beam is focused onto the surface 21.

Figure 1A:
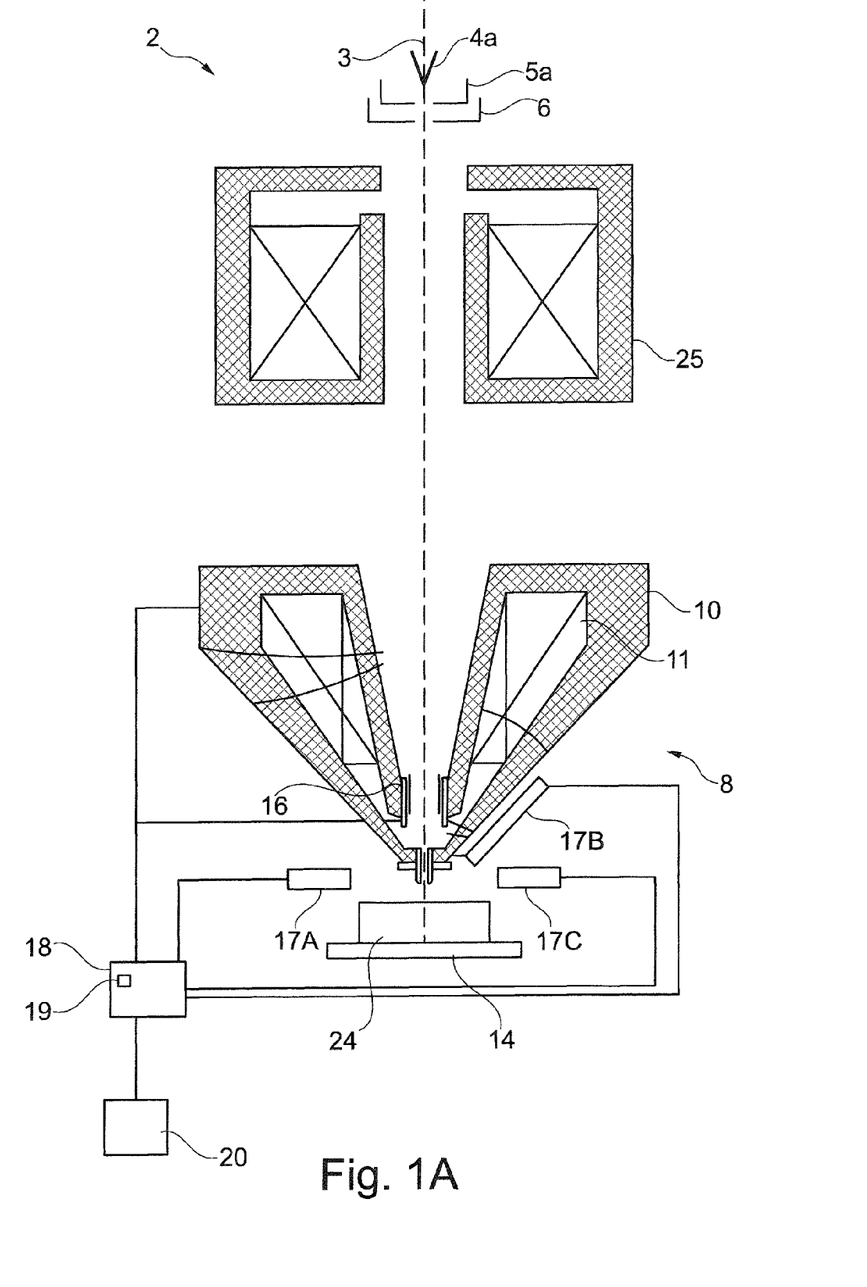
FIG. 1A shows a schematic illustration of a further embodiment of the charged particle beam device according to the invention.

FIG. 1A shows a further schematic illustration of a charged particle beam device 1. FIG. 1A is based on FIG. 1. Identical components are identified by identical reference signs. The charged particle beam device 1 is a SEM comprising a charged particle beam column 2 which is embodied as an electron beam column. The charged particle beam column 2 has an optical axis 3, a beam generator 4A in the form of a cathode filament (electron source), a first electrode 5A in the form of a Wehnelt electrode and a second electrode 6 in the form of an anode which is connected to the ground potential of the particle beam device 1. The beam generator 4A is heated for emitting electrons. The electrons are accelerated due to a potential difference between the beam generator 4A and the second electrode 6. The first electrode 5A is negatively biased with respect to the potential of the beam generator 4A for controlling the current of the beam of electrons emitted from the beam generator 4A. A condenser lens 25 is arranged between the second electrode 6 and the objective lens 8. The embodiment shown in FIG. 1A also comprises the first detector 17A, the second detector 17B and the third detector 17C. However, the second detector 17B is now arranged at the side of the objective lens within the sample chamber. Moreover, the further two detectors, namely the first detector 17A and the third detector 17C are arranged within the sample chamber.

Figure 2:
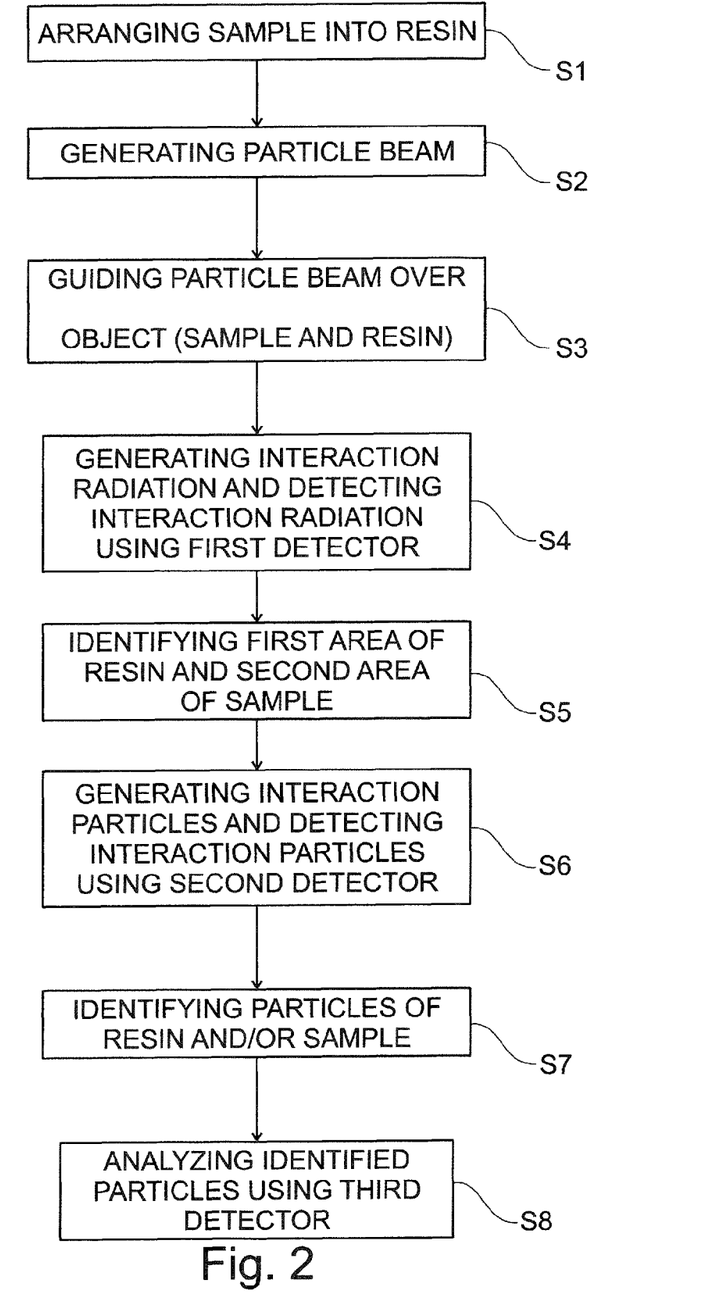
FIG. 2 shows a schematic illustration of a flowchart of an exemplary embodiment of the method according to the invention.
Figure 3:
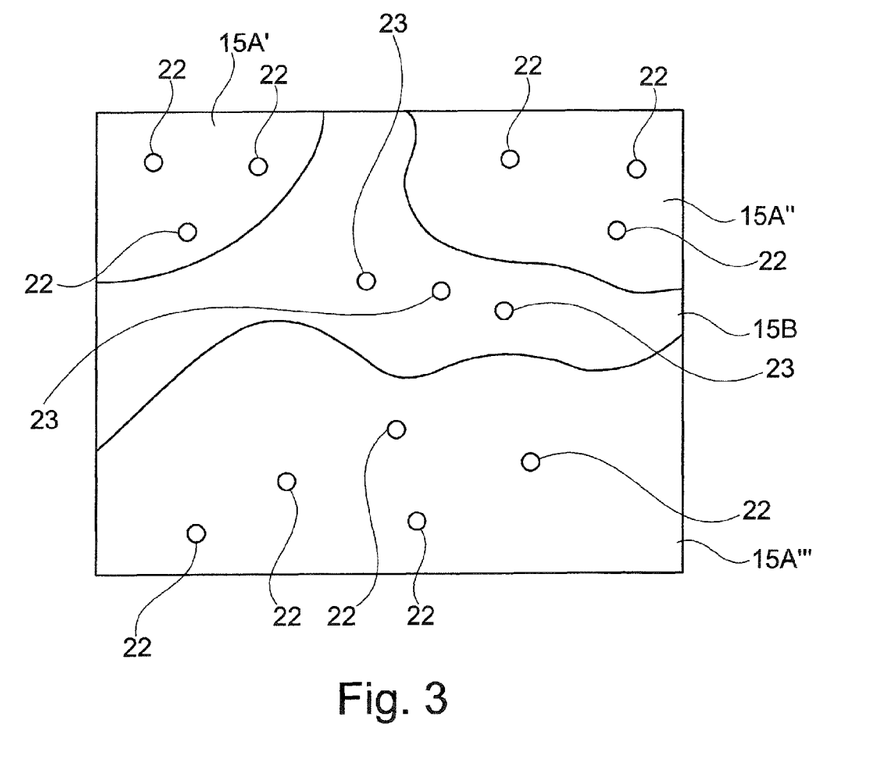
FIG. 3 shows an object of a sample to be analyzed and a resin.

FIG. 2 shows a schematic illustration of a flowchart of an exemplary embodiment of the method according to the invention. In a first step S1, the sample 15A is arranged in the bedding of the resin 15B such that the above mentioned object 24 comprising the sample 15A and the bedding of the resin 15B is generated. The object 24 comprising the sample 15A and the bedding of the resin 15B is shown in a schematic illustration in FIG. 3. FIG. 3 shows a top view of the surface 21 (see FIG. 1) of the object 24 comprising the sample 15A and the bedding of the resin 15B. Three areas of pieces of the sample 15A (for example three pieces of coal) are partly visible (or shown) and are embedded in the resin 15B. The three areas of pieces are denoted with reference signs 15A', 15A" and 15A'''. The resin 15B fixes the three pieces 15A', 15A" and 15A''' of the sample 15A relative to the resin 15B and, therefore, ensures an easy handling and/or transport or arranging of the sample 15A on the sample carrier 14 of the charged particle beam device 1.

The charged particle beam is generated in a further step S2 and is guided over an area of the object 24 comprising the sample 15A (i.e. over the pieces 15A', 15A" and 15A''' of the sample 15A) as well as the resin 15B so that the sample 15A and the resin 15B are scanned in a raster-like manner (step S3). Interaction radiation in the form of cathodoluminescence light is generated due to interaction of the charged particle beam with the sample 15A and the resin 15B. The cathodoluminescence light is detected using the first detector 17A (step S4). The resin 15B is a strong emitter of cathodoluminescence light as compared to the sample 15A to be analyzed. Therefore, it is possible to identify the first area in which the resin 15B is arranged and second areas in which the pieces 15A', 15A" and 15A''' of the sample 15A are arranged (step S5). Therefore, in turn, it is possible to create a map including the position of the areas in which the sample 15A is located and the area in which the resin 15B is located.

A step S6 is carried out after step S5 or in parallel to step S4. Step S6 comprises the step of generating interaction particles by interaction of the charged particle beam with the sample 15A (i.e. the pieces 15A', 15A" and 15A''' of the sample 15A) and the resin 15B. The interaction particles may be secondary particles (such as secondary electrons) and/or backscattered particles (such as backscattered electrons). The interaction particles are detected by using the second detector 17B. The second detector 17B generates signals which are used to record and/or display an image of the surface 21 of the scanned area of the object 24. In a further step S7, particles, for example minerals, which are included in the sample 15A (i.e. the pieces 15A', 15A" and 15A''' of the sample 15A) or in the resin 15B are identified using the image of the surface 21. The interaction of the charged particle beam with those particles generates a different signal in the second detector 17B than the rest of the sample 15A and the resin 15B. Therefore, it is possible to identify those particles in the image of the surface 21. FIG. 3 shows several particles 22 in the form of minerals included in the pieces 15A', 15A" and 15A''' of the sample 15A. FIG. 3 also shows several particles 23 in the form of minerals included in the resin 15B.

As mentioned above, step 5 provides for identifying the first area in which the resin 15B is arranged and second areas in which the pieces 15A', 15A" and 15A''' of the sample 15A are arranged. In other words, step 5 provides the position of the first area in which the resin 15B is arranged and of the second areas in which the pieces 15A', 15A" and 15A''' of the sample 15A are arranged. Therefore, it is now also possible to identify the position of the particles identified in step S7 in the pieces 15A', 15A" and 15A''' of the sample 15A or in the resin 17B.

Step S8 provides now the step of analyzing the identified particles 22 or 23 using the third detector 17C. The charged particle beam is guided to the position of each particle 22 or 23 or is guided over the surface of each particle 22 or 23. The charged particle beam interacts with the particle 22 or 23. Interaction radiation in the form of X-rays is generated and is detected by using the third detector 17C. Signals of the third detector 17C are used for generating a spectrum for each particle 22 or 23 comprised in the resin 15B and/or in the sample 15A. The composition of at least one of the particles 22 or 23 comprised in the resin 15B and/or in the sample 15A is identified by analyzing the spectrum generated for this one particle 22 or 23.

In addition to the identification and analysis of the particles in steps 7 and 8, the shape, the size and the area of these identified particles 22 and 23 can be measured and stored for further analysis using the recorded and/or displayed images of the surface 21 of the scanned area of the object 24. Such data can be used to calculate the content of particles in the object 24, in the sample 15A or in the resin 15B, and in such a way, for example, the content of minerals in coal can be determined and arrangements can be made to reduce the negative side effects at a power plant during the combustion of such a type coal as discussed earlier.

The invention has been described with reference to the drawings for embodiments in which the charged particle beam device is an electron beam device. However, instead of an electron beam device, the charged particle beam device may also be an ion beam device. The ion beam device may comprise a charged particle source in the form of an ion source, in particular a gas field ion source. Additionally or alternatively to a magnetic objective lens, an electrostatic objective lens may be provided, the electrostatic objective lens comprising several electrodes biased with different electrostatic potentials and focusing the ion beam on the object 24. This electrostatic objective lens may comprise additional electrodes biased with electrical potentials to scan the ion beam perpendicularly to the optical axis of the objective lens across the surface of the object.

The features of the invention disclosed in the description, the figures and/or the claims may be essential either individually or in any combination for the realisation of the invention in its different embodiments.

LIST OF REFERENCE SIGNS 1 charged particle beam device
2 charged particle beam column
3 optical axis
4 beam generator (thermal field emitter)
4A beam generator (cathode filament)
5 first electrode (extraction electrode)
5A first electrode (Wehnelt electrode)
6 second electrode (anode)
7 beam guiding tube
8 objective lens
9 sample chamber
10 pole pieces
11 coil
12 tube electrode
13 single electrode
14 sample carrier
15A sample
15A' first piece of sample
15A" second piece of sample
15A''' third piece of sample
15B resin
16 scanning device
17A first detector
17B second detector
17C third detector
18 electronic unit
19 microprocessor
20 monitor
21 surface
22 minerals in sample
23 minerals in resin
24 object
25 condenser lens

The invention claimed is:

1. A method of analyzing an object using a charged particle beam device, the charged particle beam device comprising a charged particle source to generate a charged particle beam, an objective lens to focus the charged particle beam onto the object, a first detector to detect interaction radiation and a second detector to detect interaction particles, the object comprising a sample and a resin, the method comprising:
generating the charged particle beam using the charged particle source;
using the objective lens to guide the charged particle beam onto the sample and the resin;
guiding the charged particle beam over the sample and the resin;
generating interaction radiation emitted from the sample and the resin due to interaction of the charged particle beam with the sample and the resin;
detecting the interaction radiation using the first detector to identify a first area in which the resin is arranged and to identify a second area in which the sample is arranged;
identifying a position of at least one particle of the resin in the first area or at least one particle of the sample in the second area by detecting interaction particles using the second detector, the interaction particles being generated by the interaction of the charged particle beam with the at least one particle of the resin or the at least one particle of the sample; and
using the charged particle beam to analyze the at least one particle of the resin or the at least one particle of the sample.

2. The method of claim 1, wherein the interaction radiation comprises cathodoluminescence light.

3. The method of claim 1, wherein analyzing the at least one particle of the resin or the at least one particle of sample comprises detecting the interaction particles using the second detector.

4. The method of claim 3, wherein the interaction particles comprise particles emitted by the sample or particles backscattered from the sample.

5. The method of claim 1, wherein analyzing the at least one particle of the resin or the at least one particle of the sample comprises detecting electromagnetic radiation emitted by the at least one particle of the resin or the at least one particle of the sample, the electromagnetic radiation being generated by the interaction of the charged particle beam with the at least one particle of the resin or the at least one particle of the sample.

6. The method of claim 5, wherein the electromagnetic radiation comprises X-rays.

7. The method of claim 1, wherein the charged particle beam comprises an electron beam.

8. The method of claim 1, wherein:
the charged particle beam comprises an electron beam;
the interaction radiation comprises cathodoluminescence light; and
analyzing the portion of the resin or the portion of the sample comprises detecting the interaction particles using the second detector.

9. The method of claim 1, wherein:
the charged particle beam comprises an electron beam;
the interaction radiation comprises cathodoluminescence light; and
analyzing the at least one particle of the resin or the at least one particle of the sample comprises detecting electromagnetic radiation emitted by the at least one particle of the resin or the at least one particle of the sample.

10. A method of analyzing an object which comprises a sample and a resin, the method comprising:
detecting interaction radiation emitted by the object to identify a first region of the object which comprises the resin and a second region of the object which comprises the sample, the interaction radiation being generated by scanning a charged particle beam over the object;
detecting interaction particles to identify a position of a portion of the sample or a portion of the resin, the interaction particles being generated by the interaction of the charged particle beam with the portion of the sample or the portion of the resin; and
using the charged particle beam to analyze the portion of the resin or the portion of the sample.

11. The method of claim 10, wherein the interaction radiation is detected with a first detector, and the interaction particles are detected with a second detector.

12. The method of claim 11, wherein analyzing the portion of the resin or the portion of the sample comprises detecting the interaction particles with the second detector.

13. The method of claim 12, wherein the interaction particles comprise particle emitted by the sample or particles backscattered from the sample.

14. The method of claim 10, wherein analyzing the portion of the resin or the portion of the sample comprises detecting electromagnetic radiation emitted by the portion of the resin or the portion of the sample, the electromagnetic radiation being generated by the interaction of the charged particle beam with the portion of the resin or the portion of the sample.

15. The method of claim 10, wherein the charged particle beam comprises an electron beam or an ion beam.

16. The method of claim 10, wherein the interaction radiation comprises cathodoluminescence light.

17. The method of claim 10, wherein:
the charged particle beam comprises an electron beam;
the interaction radiation comprises cathodoluminescence light; and
analyzing the portion of the resin or the portion of the sample comprises detecting the interaction particles.

18. The method of claim 10, wherein:
the charged particle beam comprises an electron beam;
the interaction radiation comprises cathodoluminescence light; and
analyzing the portion of the resin or the portion of the sample comprises detecting electromagnetic radiation emitted by the portion of the resin or the portion of the sample.

19. A computer program product tangibly embodied in a computer readable medium comprising instructions configured to cause a computing device to analyze an object using a charged particle beam device,
wherein the instructions are configured to cause the computing device to execute the method according to claim 1.

20. A device, comprising:
a charged particle source configured to generate a charged particle beam;
an objective lens configured to focus the charged particle beam onto an object;
a first detector configured to detect interaction radiation;
a second detector configured to detect interaction particles;
a microprocessor; and
a computer readable medium according to claim 19.

* * * * *

UNITED STATES PATENT AND TRADEMARK OFFICE
CERTIFICATE OF CORRECTION

| | | |
|---|---|---|
| PATENT NO. | : 9,159,532 B2 | Page 1 of 1 |
| APPLICATION NO. | : 14/150012 | |
| DATED | : October 13, 2015 | |
| INVENTOR(S) | : Edward Hill and Stewart Bean | |

It is certified that error appears in the above-identified patent and that said Letters Patent is hereby corrected as shown below:

Col. 1, line 4, under title, insert

-- Cross-Reference to Related Applications

This application claims priority under 35 U.S.C. §119 to European Application No. 13 151 344.2, filed Jan. 15, 2013, the entire contents of which are hereby incorporated by reference. --.

Signed and Sealed this
Sixteenth Day of February, 2016

Michelle K. Lee
*Director of the United States Patent and Trademark Office*